(12) United States Patent
Guillon et al.

(10) Patent No.: US 7,838,456 B2
(45) Date of Patent: Nov. 23, 2010

(54) MODIFIED EU-1 ZEOLITE AND ITS USE IN THE ISOMERIZATION OF AROMATIC C8 COMPOUNDS

(75) Inventors: Emmanuelle Guillon, Vernaison (FR); Erie Sanchez, Saint Genis Laval (FR)

(73) Assignee: IFP Energies Nouvelles, Rueil Malmaison Cedex (FR)

( * ) Notice: Subject to any disclaimer, the term of this patent is extended or adjusted under 35 U.S.C. 154(b) by 256 days.

(21) Appl. No.: 12/107,224

(22) Filed: Apr. 22, 2008

(65) Prior Publication Data

US 2008/0281138 A1 Nov. 13, 2008

(30) Foreign Application Priority Data

Apr. 23, 2007 (FR) .................................. 07 02943

(51) Int. Cl.
*B01J 29/06* (2006.01)
*B01J 29/72* (2006.01)
*B01J 29/74* (2006.01)

(52) U.S. Cl. .............................. 502/60; 502/73; 502/74; 423/700; 585/481

(58) Field of Classification Search .................. 502/60, 502/73, 74; 423/700; 585/481
See application file for complete search history.

(56) References Cited

U.S. PATENT DOCUMENTS

| 4,537,754 A | * | 8/1985 | Casci et al. | .................. 423/708 |
| 4,695,667 A | | 9/1987 | Sumitani et al. | |
| 6,733,658 B2 | * | 5/2004 | Benazzi et al. | .......... 208/111.01 |
| 2003/0127356 A1 | | 7/2003 | Benazzi et al. | |
| 2007/0117711 A1 | * | 5/2007 | Caullet et al. | .................. 502/60 |

FOREIGN PATENT DOCUMENTS

FR 2 765 209 A1 12/1998

OTHER PUBLICATIONS

G.N. Rao et al., "Thermal and Hydrothermal Stabilities of Zeolite EU-1", Applied Catalysis A: General 119 (1994) pp. 33-43.

* cited by examiner

*Primary Examiner*—David M Brunsman
(74) *Attorney, Agent, or Firm*—Millen, White, Zelano & Branigan, P.C.

(57) ABSTRACT

A catalyst is described which comprises at least one modified EU-1 zeolite containing silicon atoms and aluminum atoms, at least one matrix and at least one metal from group VIII of the periodic table of the elements, the modified zeolite having a number of hexacoordinated aluminum atoms representing more than 20% by weight of the total number of aluminum atoms present in said modified EU-1 zeolite. Said catalyst is used in a process for the isomerization of an aromatic feed comprising at least one compound containing eight carbon atoms per molecule.

23 Claims, No Drawings

MODIFIED EU-1 ZEOLITE AND ITS USE IN THE ISOMERIZATION OF AROMATIC C8 COMPOUNDS

The present invention relates to a catalyst comprising an EU-1 zeolite with a modified zeolitic framework. More precisely, said EU-1 zeolite has tetracoordinated aluminium atoms and hexacoordinated aluminium atoms in a well determined proportion by weight. Said catalyst advantageously has its application in a process for isomerizing an aromatic cut comprising at least one aromatic compound containing eight carbon atoms per molecule. Said cut is a feed containing a mixture of xylenes, or ethylbenzene alone or a mixture of xylene and ethylbenzene. This feed is usually termed an "aromatic C8 cut".

PRIOR ART

Catalysis of the isomerization of an aromatic C8 cut, for example ethylbenzene, into xylenes has formed the subject matter of a number of patents. A number of zeolitic catalysts have been proposed to catalyze such a reaction. Zeolites used for isomerizing a C8 aromatic cut include ZSM-5, used alone or mixed with other zeolites such as mordenite, for example. Those catalysts have been described in U.S. Pat. No. 4,467, 129, U.S. Pat. No. 4,482,773 and EP-B 0 013 617. Other catalysts principally based on mordenite have been described in U.S. Pat. No. 4,723,051, U.S. Pat. No. 4,665,258 and FR-A-2 477 903. More recently, a catalyst based on a zeolite with structure type EUO (EP-A1-0 923 987) has been proposed, as well as a catalyst based on a zeolite with structure type MTW (WO-A-2005/065380).

The majority of those zeolitic catalysts, while producing an advantageous selectivity for xylenes, does not provide an optimum xylenes yield because the conversion of the aromatic C8 cut, especially ethylbenzene, is too low.

One of the aims of the present invention is to provide a novel catalyst based on an EU-1 zeolite which is more active than known prior art zeolitic catalysts while also being selective for the production of xylenes, to improve not only the conversion of the feed to be isomerized but also the yield of desired products which are constituted by the xylenes.

SUMMARY AND ADVANTAGE OF THE INVENTION

The present invention concerns a catalyst which comprises at least one modified EU-1 zeolite containing silicon atoms and aluminium atoms, at least one matrix and at least one metal from group VIII of the periodic table of the elements, said catalyst being characterized in that the number of hexacoordinated aluminium atoms present in said modified zeolite represents more than 20% by weight of the total number of aluminium atoms present in said modified EU-1 zeolite.

Said catalyst of the invention is advantageously used in a process for isomerization of an aromatic cut comprising at least one aromatic compound containing eight carbon atoms per molecule.

It has surprisingly been discovered that a catalyst in the form of beads or extrudates comprising at least one matrix, at least one metal from group VIII of the periodic table of the elements and at least one EU-1 zeolite wherein the number of hexacoordinated aluminium atoms represents more than 20% by weight of the total number of aluminium atoms present in said modified zeolite results in improved catalytic performances as regards the conversion of an aromatic feed to be isomerized when said catalyst is used in a process for isomerizing an aromatic cut comprising at least one aromatic compound containing eight carbon atoms per molecule. Such a catalyst is substantially more active than a catalyst comprising unmodified EU-1 zeolite which has a number of hexacoordinated aluminium atoms representing less than 20% by number of the total number of aluminium atoms present in the unmodified zeolite. Further, since the selectivity for desired products, namely xylenes, is maintained when using a catalyst comprising a modified EU-1 zeolite, there is an increase in the yield of xylenes when the isomerization process is carried out in the presence of a catalyst in accordance with the invention.

DETAILED DESCRIPTION OF THE INVENTION

The present invention pertains to a catalyst which comprises at least one modified EU-1 zeolite containing silicon atoms and aluminium atoms, at least one matrix and at least one metal from group VIII of the periodic table of the elements, said catalyst being characterized in that the number of hexacoordinated aluminium atoms present in said modified zeolite represents more than 20% by weight of the total number of aluminium atoms present in said modified EU-1 zeolite.

In accordance with the invention, the modified EU-1 zeolite in the catalyst of the invention has a number of hexacoordinated aluminium atoms, denoted $Al_{VI}$, representing more than 20% by weight, preferably more than 22% by weight, more preferably more than 25% by weight and still more preferably more than 30% by weight of the total number of aluminium atoms present in said modified zeolite. The aluminium atoms present in said EU-1 zeolite in the catalyst of the invention and which is not in the hexacoordinated aluminium form are present in the form of tetracoordinated aluminium atoms, denoted $Al_{IV}$. Said tetracoordinated aluminium atoms are present in the zeolitic framework, while the hexacoordinated aluminium atoms are present outside the zeolitic framework (extra-lattice aluminium). In particular, at least some of said hexacoordinated aluminium atoms are found in the pores of the modified EU-1 zeolite.

In accordance with the invention, the percentage by weight of tetracoordinated and hexacoordinated aluminium atoms present in the modified EU-1 zeolite is determined by solid $^{27}Al$ nuclear magnetic resonance. Aluminium NMR is known for its use in characterizing and quantifying the various coordination states of this nucleus ("Analyse physico-chimiques des catalyseurs industriels" [Physico-chemical analyses of industrial catalysts], J Lynch, Technip (2001), Chapter 13, pages 290 and 291). The aluminium NMR spectrum of modified EU-1 zeolite exhibits two signals, one being characteristic of the resonance of tetracoordinated aluminium atoms and the other being characteristic of the resonance of hexacoordinated aluminium atoms. Tetracoordinated $Al_{IV}$ aluminium atoms resonate at a chemical displacement in the range +40 ppm to +75 ppm and hexacoordinated $Al_{VI}$ aluminium atoms resonate at a chemical displacement in the range −15 ppm to +15 ppm. The percentage by weight of the two aluminium species $Al_{IV}$ and $Al_{VI}$ is quantified by integrating the signals corresponding to each of these species.

More precisely, the modified EU-1 zeolite present in the catalyst of the invention was analyzed by solid $^{27}Al$ MAS-NMR on an Avance type Brucker spectrometer, 400 MHz, using a 4 mm probe optimized for $^{27}Al$. The rate of rotation of the sample was close to 14 kHz. The aluminium atom is a quadripolar nucleus with a spin of 5/2. Under "selective" analysis conditions, namely a low radiofrequency field of 30 kHz, a low pulse angle of π/2 and in the presence of a watersaturated sample, the magic angle spinning (MAS) NMR technique, denoted MAS-NMR, is a quantitative technique. Decomposition of each MAS-NMR spectrum provides direct access to the quantity of the various aluminium species, namely the tetracoordinated aluminium atoms $Al_{IV}$ and the hexacoordinated aluminium atoms $Al_{VI}$. Each spectrum is characterized by the chemical displacement with respect to a 1M aluminium nitrate solution which has an aluminium signal at zero ppm. The signals characterizing the tetracoordinated aluminium atoms $Al_{IV}$ are integrated between +40 ppm and +75 ppm, which corresponds to area 1, and the signals characterizing the hexacoordinated aluminium atoms $Al_{VI}$ are integrated between −15 ppm and +15 ppm, which corresponds to area 2. The percentage by weight of hexacoordinated aluminium atoms $Al_{VI}$ is equal to the ratio: area 2/(area 1+area 2).

The modified EU-1 zeolite included in the catalyst of the invention and containing aluminium atoms and silicon atoms has an overall Si/Al atomic ratio in the range 5 to 100, preferably in the range 10 to 50 and more preferably in the range 10 to 35. In accordance with the invention, said overall Si/Al atomic ratio of said modified EU-1 zeolite advantageously does not vary by more than plus or minus 2% about the overall Si/Al atomic ratio of the as-synthesized EU-1 zeolite from which said modified zeolite is derived and highly advantageously said overall Si/Al atomic ratio of said modified EU-1 remains unchanged compared with that of the as-synthesized EU-1 zeolite. The overall Si/Al atomic ratio, determined by X ray fluorescence or by atomic absorption, includes both the aluminium atoms present in the zeolitic framework and any aluminium atoms which may be present outside the zeolitic framework, also termed the extra-lattice aluminium. Each tetracoordinated aluminium atom present in the zeolitic framework of the modified EU-1 zeolite is bonded to four oxygen atoms and is in a tetrahedral configuration. Each hexacoordinated aluminium atom present in the modified EU-1 zeolite but outside the zeolitic framework is surrounded by 6 oxygen atoms and is in an octahedral configuration. In the as-synthesized EU-1 zeolite from which the modified EU-1 is derived, the percentage by weight of tetracoordinated aluminium atoms, determined by aluminium MAS-NMR as described above, is more than 90%, preferably more than 95%, more preferably more than 98% and still more preferably it is 100%. In accordance with the invention and in accordance with a highly preferred embodiment of the invention, the overall number of aluminium atoms present in the modified EU-1 zeolite and that of the aluminium atoms present in the as-synthesized EU-1 zeolite from which the modified EU-1 zeolite is derived are identical.

The modified EU-1 zeolite present in the catalyst of the invention is highly advantageously in its protonated form (hydrogen form, $H^+$) in which the proportion of cations other than $H^+$ is less than 30% of the total number of cations, preferably less than 20% and highly preferably less than 5% with respect to the total number of cations on the zeolite.

In accordance with the invention, said catalyst comprises at least one group VIII metal selected from iron, cobalt, nickel, ruthenium, rhodium, palladium, osmium, iridium and platinum, preferably selected from noble metals from group VIII, more preferably selected from palladium and platinum and still more preferably it is platinum. The dispersion of the group VIII metal(s), determined by chemisorption, for example by $H_2$—$O_2$ titration or by chemisorption of carbon monoxide, is in the range 50% to 100%, preferably in the range 60% to 100% and more preferably in the range 70% to 100%. The macroscopic distribution coefficient of the group VIII metal(s), obtained from its profile determined by Casta-ing microprobe, defined as the ratio of the concentrations of the group VIII metal(s) at the grain core with respect to the edge of that grain, is in the range 0.7 to 1.3, preferably in the range 0.8 to 1.2. A value of this ratio of close to 1 is evidence of the homogeneity of the distribution of the group VIII metal(s) in the catalyst.

Said catalyst advantageously comprises at least one additional metal selected from the group formed by metals from groups IIIA, IVA and VIIB of the periodic table of the elements, preferably selected from gallium, indium, tin and rhenium. Said additional metal is preferably selected from indium, tin and rhenium.

Said catalyst also advantageously includes sulphur.

More particularly, said catalyst of the invention contains:
- 1% to 90%, preferably 3% to 80% and more preferably 4% to 60% by weight, of said modified EU-1 zeolite;
- 0.01% to 4%, preferably 0.05% to 2.0% by weight, of at least one metal from group VIII of the periodic table of the elements;
- optionally, 0.01% to 2%, preferably 0.05% to 1% by weight of at least one additional metal selected from the group formed by metals from groups IIIA, IVA and VIIB;
- optionally, a sulphur content such that the ratio of the number of atoms of sulphur to the number of atoms of metal(s) from group VIII is in the range 0.5:1 to 2:1;
- at least one matrix providing the complement to 100% in the catalyst.

The matrix forming part of the composition of the catalyst of the invention is selected from clays, magnesia, aluminas, silicas, titanium oxide, boron oxide, zirconia, aluminium phosphates, titanium phosphates, zirconium phosphates, silica-aluminas and coal or a mixture of at least two of these compositions. Preferably, the matrix is an alumina.

Said catalyst is in the form of beads or extrudates, preferably in the form of extrudates.

The present invention also pertains to the preparation of the catalyst of the invention. An essential step in the preparation of the catalyst of the invention consists of carrying out a heat treatment in the presence of steam on an EU-1 zeolite which may or may not have been formed, as-synthesized or free of organic template. Said heat treatment in the presence of steam results in a modification of the zeolitic framework of the EU-1 zeolite which undergoes said treatment so that the number of hexacoordinated aluminium atoms in the modified EU-1 zeolite represents more than 20% by weight, preferably more than 22% by weight, more preferably more than 25% by weight and still more preferably more than 30% by weight of the total number of aluminium atoms present in said modified zeolite. Highly preferably, the preparation of the catalyst does not include any step in which the EU-1 zeolite undergoes a treatment with an acid solution.

A first implementation of the preparation of the catalyst of the invention consists of a process comprising at least the following steps:
- a1) synthesizing at least one EU-1 zeolite having an overall Si/Al atomic ratio in the range 5 to 100, preferably in the range 10 to 50 and still more preferably in the range 10 to 35;
- b1) heat treating the zeolite from said step a1) in the presence of steam to obtain a modified EU-1 zeolite;
- c1) forming said modified EU-1 zeolite with a matrix to form a modified zeolitic support;
- d1) depositing at least one metal from group VIII of the periodic table of the elements, the order of carrying out said steps c1) and d1) being of no consequence after said step b1).

A second implementation of the preparation of the catalyst of the invention consists of a process comprising at least the following steps:

a2) synthesizing at least one EU-1 zeolite having an overall Si/Al atomic ratio in the range 5 to 100, preferably in the range 10 to 50 and still more preferably in the range 10 to 35;

b2) forming the EU-1 zeolite derived from said step a2) with a matrix to form a zeolitic support;

c2) heat treating the zeolite formed in step b2) in the presence of steam;

d2) depositing at least one metal from group VIII of the periodic table of the elements on the modified zeolitic support from step c2).

A third implementation of the preparation of the catalyst of the invention consists of a process comprising at least the following steps:

a3) synthesizing at least one EU-1 zeolite having an overall Si/Al atomic ratio in the range 5 to 100, preferably in the range 10 to 50 and still more preferably in the range 10 to 35;

b3) forming the EU-1 zeolite derived from said step a3) with a matrix to form a zeolitic support;

c3) depositing at least one metal from group VIII of the periodic table of the elements on the modified zeolitic support from step b3);

d3) heat treating the zeolitic support impregnated with at least one said group VIII metal from said step c3) in the presence of steam.

In accordance with the invention, the initial zeolite which has not yet been modified for inclusion in the catalyst of the invention as prepared in steps a1), a2) or a3) has a microporous one-dimensional framework with a pore diameter of 4.1×5.4 Å (1 Å=1 Angstrom=$10^{-10}$ m) ("Atlas of zeolite framework types", Ch Baerlocher, W M Meier and D H Olson, $5^{th}$ edition, 2001). Further, N A Briscoe et al have disclosed, in an article in the review Zeolites (1988, 8, 74), that these one-dimensional channels have side pockets with a depth of 8.1 Å and a diameter of 6.8×5.8 Å. The physicochemical characteristics of said EU-1 zeolite have already been described in EP-B1-0 042 226.

To synthesize EU-1 zeolite in accordance with said step a1), a2) or a3), the skilled person will initially refer to the teaching of EP-B1-0 042 226 which describes the synthesis of an as-synthesized EU-1 zeolite.

More precisely, to prepare an EU-1 zeolite according to said step a1), a2) or a3), the following are mixed in an aqueous medium: at least one source of silicon source, at least one source of aluminium, at least one nitrogen-containing organic template with formula $R_1R_2R_3-N^+-(CH_2)_n-N^+-R_4R_5R_6$ in which n is in the range 3 to 12, groups $R_1$ to $R_6$, which may be identical or different, are alkyl groups containing 1 to 8 carbon atoms, up to five of said groups $R_1$ to $R_6$ possibly being hydrogen, and optionally zeolitic seeds.

The reaction mixture has the following molar composition:
$SiO_2/Al_2O_3$: 10-150
$OH^-/SiO_2$: 0.1-6;
$(M^++Q)/Al_2O_3$: 0.5-100;
$Q/(M^++Q)$: 0.1-10;
$H_2O/SiO_2$: 1-100.

Q is the cation $R_1R_2R_3-N^+-(CH_2)_n-N^+-R_4R_5R_6$ described above, preferably 1,6-N,N,N,N',N',N',-hexamethylhexamethylene diammonium and $M^+$ is an alkali or ammonium cation.

Said reaction mixture is reacted under autogenous pressure, optionally with addition of a gas, for example nitrogen, at a temperature in the range 85° C. to 250° C. until crystals of the EU-1 zeolite are formed. The reaction period is in the range from 1 minute to a few months depending on the composition of the reagents, the mode of heating and mixing, the reaction temperature and the stirring mode. At the end of the reaction, the solid phase is collected on a filter and washed. At this stage, the EU-1 zeolite is termed "as-synthesized" and contains in its intra-crystalline pores at least the cation $R_1R_2R_3-N^+-(CH_2)_n-N^+-R_4R_5R_6$, preferably 1,6-N,N,N,N',N',N',-hexamethylhexamethylene diammonium. In accordance with the invention, said as-synthesized EU-1 zeolite obtained at the end of step a1), a2) or a3) has an overall Si/Al atomic ratio in the range 5 to 100, preferably in the range 10 to 50 and more preferably in the range 10 to 35. The overall Si/Al atomic ratio, determined by X ray fluorescence or atomic absorption, takes into account both the aluminium atoms present in the zeolitic framework and any aluminium atoms which may be present outside said zeolitic framework, also termed extra-lattice aluminium. The percentage by weight of tetracoordinated aluminium atoms present in the as synthesized EU-1 zeolite prepared using said step a1), a2) or a3), determined by MAS-NMR aluminium analysis as described above in the present description, is more than 90%, preferably more than 95%, more preferably more than 98% and still more preferably it is equal to 100%.

In accordance with the first implementation of the preparation of the catalyst of the invention, the as-synthesized EU-1 zeolite from said step a1) undergoes calcining in a stream of dry air, at a temperature in the range 400° C. to 600° C., then it undergoes at least one heat treatment in the presence of steam in step b1). The calcining period can vary and is in the range from a few hours to a few days. The calcining treatment prior to said step b1) of said EU-1 zeolite from said step a1) is intended to eliminate the organic template present in the micropores of the zeolite, for example the cation $R_1R_2R_3-N^+-(CH_2)_n-N^+-R_4R_5R_6$, preferably 1,6-N,N,N,N',N',N',-hexamethylhexamethylene diammonium. More preferably, one or more ion exchange steps using at least one $NH_4NO_3$ solution is (are) carried out between calcining in a stream of dry air and heat treatment carried out in the presence of steam to eliminate at least part, preferably practically all of the alkali cation, in particular sodium, which may be present in the cationic position in the as-synthesized zeolite. Each exchange step is carried out at a temperature which is preferably in the range 50° C. to 150° C. for a period which is advantageously in the range from 2 hours to 10 hours. In general, an aqueous solution of ammonium nitrate $NH_4NO_3$ with a normality in the range 7N to 12N is used. Similarly, at the end of said heat treatment step b1), it is possible to carry out one or more ion exchange step(s) using at least one $NH_4NO_3$ solution, to eliminate residual alkali cations and in particular sodium.

The EU-1 zeolite from said step a1), calcined and preferably exchanged so that it is in its $NH_4$ form, undergoes at least one heat treatment in the presence of steam in accordance with step b1) of the first implementation of the preparation of the catalyst of the invention. The operating conditions for the heat treatment in the presence of steam, in particular the temperature and duration of said treatment and the volume percentage of the steam, are adapted to obtain a modified EU-1 zeolite wherein the number of hexacoordinated aluminium atoms represents more than 20% by weight of the total number of aluminium atoms present in said modified zeolite. Advantageously, the heat treatment carried out in the presence of steam is carried out at a temperature in the range 200° C. to 470° C., preferably in the range 320° C. to 460° C. Said heat treatment generally lasts 0.5 hours or more, preferably in the range 0.5 hours to 24 hours, and highly preferably in the range 1 hour to 12 hours. The volume percentage of the steam during the heat treatment is generally in the range 5% to 100%, preferably in the range 20% to 100%, and more preferably in the range 40% to 100%. The optional volume fraction other than the steam is formed by air. The flow rate of the gas formed by steam and optionally by air is advantageously in the range 0.2 l/h/g of zeolite to 10 l/h/g of zeolite. The heat treatment in the presence of steam may be carried out as many times as is necessary to obtain the modified EU-1 zeolite having the desired characteristics, in particular a number of hexacoordinated aluminium atoms representing more than 20% by weight of the total number of aluminium atoms present in said zeolite. The number of heat treatments carried out in said step b1) is preferably less than 4 and advantageously a single heat treatment according to said step b1) is carried out.

The preparation of the catalyst in accordance with the first implementation is continued by carrying out said forming step c1) and by carrying out said step d1) for depositing at least one metal from group VIII of the periodic table of the elements. The order of carrying out said steps c1) and d1), subsequent to said step b1), is of no consequence. Preferably, said step c1) precedes said step d1).

To carry out said step c1) for forming said modified EU-1 zeolite, a matrix is used which is selected from clays, magnesia, aluminas, silicas, titanium oxide, boron oxide, zirconia, aluminium phosphates, titanium phosphates, zirconium phosphates, silica-aluminas and coal or a mixture of at least two of these compositions. Preferably, the matrix is an alumina. Advantageously, the modified EU-1 zeolite associated with the matrix is formed into beads or extrudates, highly advantageously into the form of extrudates. The modified EU-1 zeolite-matrix ensemble constitutes the modified zeolitic support of the catalyst of the invention.

More particularly, forming in accordance with said step c1) consists of mixing the modified EU-1 zeolite in a moist matrix gel, preferably alumina, generally obtained by mixing at least one acid and a matrix powder for the period necessary to obtain good homogeneity of the paste, i.e. for about ten minutes, for example, then passing the paste obtained through a die to form extrudates, for example with a diameter of 0.4 to 4 mm. Forming is generally followed by drying then calcining. Drying is advantageously carried out at a temperature in the range 100° C. to 150° C. for a period in the range 5 to 20 hours in an oven. Calcining is advantageously carried out at a temperature in the range 250° C. to 600° C. for a period in the range 1 to 8 hours.

Step d1) for preparing the catalyst comprising a modified EU-1 zeolite consists of introducing at least one metal from group VIII of the periodic table of the elements and optionally at least one metal selected from metals from groups IIIA, IVA and VIIB.

Said group VIII metal present in the catalyst of the invention is selected from iron, cobalt, nickel, ruthenium, rhodium, palladium, osmium, iridium and platinum, preferably from the noble metals and highly preferably from palladium and platinum. More preferably, said group VIII metal is platinum. In accordance with the method for depositing said group VIII metal, as indicated below in the description, said group VIII metal, preferably platinum, may be deposited primarily on the modified zeolite or on the matrix.

Said metal selected from metals from groups IIIA, IVA and VIIB which are optionally present in the catalyst of the invention is selected from gallium, indium, tin and rhenium, preferably from indium, tin and rhenium.

After obtaining the modified EU-1 zeolite and forming it, the catalyst of the invention may be prepared using any method which is known to the skilled person. Preferably, following calcining carried out at the end of forming step c1), at least one group VIII metal is introduced onto the modified zeolitic support, namely either mainly onto the matrix or mainly onto the modified zeolite or onto the modified zeolite-matrix ensemble. Said metal is advantageously deposited on the zeolitic support using the dry impregnation technique, the excess impregnation technique or by ion exchange. When a plurality of metals are introduced, these may be introduced either all in the same manner or using different techniques.

Any group VIII metal precursor is suitable for depositing one or more of the group VIII metal(s) on the modified zeolitic support. In particular, for any noble metal from group VIII, it is possible to use ammonia compounds or compounds such as ammonium chloroplatinate, dicarbonyl platinum dichloride, hexahydroxyplatinic acid, palladium chloride or palladium nitrate. The platinum is generally introduced in the form of hexachloroplatinic acid. The group VIII noble metal is preferably introduced by impregnation using an aqueous or organic solution of one of the metallic compounds cited above. Examples of suitable organic solvents which may be cited are paraffinic, naphthenic or aromatic hydrocarbons may be cited, containing, for example, 6 to 12 carbon atoms per molecule, and halogenated organic compounds containing 1 to 12 carbon atoms per molecule, for example. Examples which may be cited are n-heptane, methylcyclohexane, toluene and chloroform. Mixtures of solvents may also be used.

Certain parameters employed during deposition, in particular the nature of the precursor of the group VIII metal(s) used, can be controlled to orientate the deposition of said metal(s) mainly on the matrix or on the modified zeolite. To introduce the group VIII metal(s), preferably platinum and/or palladium, mainly on the matrix, it is possible to carry out an anion exchange with hexachloroplatinic acid and/or hexachloropalladic acid in the presence of a competing agent, for example hydrochloric acid, deposition generally being followed by calcining, for example at a temperature in the range 350° C. to 550° C. for a period in the range 1 to 4 hours. With such precursors, the group VIII metal(s) is (are) deposited mainly on the matrix and said metal(s) are well dispersed and have good macroscopic distribution through the catalyst grain.

It is also possible to envisage depositing the group VIII metal(s), preferably platinum and/or palladium, by cation exchange so that said metal(s) are mainly deposited on the modified zeolite. Thus, in the case of platinum, the precursor may, for example, be selected from:

ammoniacal compounds such as platinum (II) tetrammine salts with formula $Pt(NH_3)_4X_2$, platinum (IV) hexammine salts with formula $Pt(NH_3)_6X_4$; platinum (IV) halogenopentammine salts with formula $(PtX(NH_3)_5)X_3$, platinum N-tetrahalogenodiammine salts with formula $PtX_4(NH_3)_2$; and halogenated compounds with formula $H(Pt(acac)_2X)$;

X being a halogen selected from the group formed by chlorine, fluorine, bromine and iodine, X preferably being chlorine, and "acac" representing the acetylacetonate group (with empirical formula $C_5H_7O_2$), derived from acetylacetone. With such precursors, the group VIII metal(s) is (are) mainly deposited on the zeolite and said metal(s) are well dispersed with good macroscopic distribution through the catalyst grain.

Dry impregnation of the group VIII metal onto the zeolitic support results in said metal being deposited both on the matrix and on the modified zeolite.

In the case in which the catalyst of the invention also contains at least one metal selected from metals from groups IIIA, IVA and VIIB, any technique for depositing such a metal which is known to the skilled person and any precursor for such metals is suitable.

The group VIII metal(s) and that (those) from groups IIIA, IVA and VIIB may be added either separately or simultaneously in at least one unitary step. When at least one metal from groups IIIA, IVA and VIIB is added separately, it is preferable that it should be added after the group VIII metal.

The additional metal selected from metals from groups IIIA, IVA and VIIB may be introduced via compounds such as chlorides, bromides or nitrates of metals from groups IIIA, IVA and VIIB, for example. As an example, in the case of indium, the nitrate or chloride is advantageously used and in the case of rhenium, perrhenic acid is advantageously used. The additional metal selected from the metals from groups IIIA, IVA and VIIB may also be introduced in the form of at least one organic compound selected from the group constituted by complexes of said metal, in particular polyketone complexes of the metal and hydrocarbylmetals such as metal alkyls, cycloalkyls, aryls, alkylaryls or arylalkyls. In this latter case, the metal is advantageously introduced using a solution of an organometallic compound of said metal in an organic solvent. It is also possible to use organohalogenated compounds of the metal. Particular examples of organic compounds of metals which may be cited are tetrabutyltin in the case of tin, and triphenylindium in the case of indium.

If the additional metal selected from metals from groups IIIA, IVA and VIIB is introduced before the group VIII metal, the compound of metal IIIA, IVA and/or VIIB employed is generally selected from the group constituted by the metal halide, nitrate, acetate, tartrate, carbonate and oxalate. Introduction is thus advantageously carried out in aqueous solution. However, it may also be introduced using a solution of an organometallic compound of a metal, for example tetrabutyltin. In this case, before introducing at least one metal from group VIII, calcining in air is carried out.

Further, intermediate treatments such as calcining and/or reduction may be carried out between successive deposits of the various metals.

The preparation of the catalyst in accordance with said first implementation is generally terminated by calcining, normally at a temperature in the range 250° C. to 600° C., for a period in the range 0.5 to 10 hours, preferably preceded by drying, for example oven drying, at a temperature from ambient temperature to 250° C., preferably 40° C. to 200° C. Said drying step is preferably carried out during the temperature ramp-up step necessary to carry out said calcining. Prior reduction of the catalyst may be carried out ex situ in a stream of hydrogen, for example at a temperature of 450° C. to 600° C., for a period of 0.5 to 4 hours.

In accordance with the second implementation of the preparation of the catalyst of the invention, the as-synthesized EU-1 zeolite obtained in step a2) is then formed with a matrix to prepare a zeolitic support in accordance with said step b2). The as-synthesized EU-1 zeolite is preferably calcined then exchanged before being formed with a matrix, preferably an alumina. However, the forming of step b2) may be carried out directly by using as-synthesized EU-1 zeolite, the calcining and ion exchange then being carried out on the formed zeolite. The as-synthesized zeolite is calcined in a stream of dry air at a temperature in the range 400° C. to 600° C. The calcining period may vary and is in the range from a few hours to a few days. The calcining treatment, prior to or subsequent to said step b2), of said EU-1 zeolite from said step a2) is intended to eliminate the organic template present in the micropores of the zeolite, for example the cation $R_1R_2R_3$—$N^+$—$(CH_2)_n$—$N^+$—$R_4R_5R_6$, preferably 1,6-N,N,N,N',N',N',-hexamethylhexamethylene diammonium. One or more ion exchange step(s) using at least one $NH_4NO_3$ solution is (are) carried out following calcining in a stream of dry air to at least partially, preferably practically completely, eliminate the alkali cation, in pa sodium, which may be present in the cationic position in the zeolite in its as-synthesized form. Each exchange is carried out at a temperature which is preferably in the range 50° C. to 150° C. for a period which is advantageously in the range 2 hours to 10 hours. In general, an aqueous solution of ammonium nitrate $NH_4\,NO_3$ with a normality of 7N to 12N is used.

The matrix employed to carry out said step b2) is selected from those described for carrying out step c1) of the first implementation for the preparation of the catalyst of the invention. Similarly, said step b2) is carried out using the same protocol (mixing, extrusion, drying then calcining) and under operating conditions analogous to those described for carrying out step c1) of the first implementation for the preparation of the catalyst of the invention. Advantageously, the EU-1 zeolite associated with the matrix is formed into beads or extrudates, preferably into extrudates, and constitutes the zeolitic support of the catalyst of the invention.

The zeolitic support obtained at the end of said step b2) contains a EU-1 zeolite the zeolitic framework of which has not yet been modified. Said support then undergoes at least one heat treatment carried out in the presence of steam in accordance with said step c2) so that the EU-1 zeolite in said zeolitic support has a number of hexacoordinated aluminium atoms representing more than 20% by weight, preferably more than 22% by weight, more preferably more than 25% by weight and still more preferably more than 30% by weight of the total number of aluminium atoms present in said zeolite.

Advantageously, the heat treatment in the presence of steam which the zeolitic support undergoes is carried out at a temperature in the range 200° C. to 470° C., preferably in the range 320° C. to 460° C. Said heat treatment generally lasts 0.5 hours or more, preferably in the range 0.5 hours to 24 hours, and highly preferably in the range 1 hour to 12 hours. The percentage by volume of steam during the heat treatment is generally in the range 5% to 100%, preferably in the range 20% to 100%, still more preferably in the range 40% to 100%. The volume fraction other than the steam which may be present is formed by air. The flow rate of the gas formed by steam and optionally by air is in the range 0.2 l/h/g of zeolitic support to 10 l/h/g of zeolitic support. The heat treatment in the presence of steam may be repeated as many times as is necessary to obtain the modified EU-1 zeolite having the desired characteristics, in particular a number of hexacoordinated aluminium atoms representing more than 20% by weight of the total number of aluminium atoms present in said zeolite. The number of heat treatments in said step c2) is preferably less than 4, and advantageously a single heat treatment is carried out in said step c2).

In accordance with the second implementation of the preparation of the catalyst of the invention, the EU-1 zeolite included in the zeolitic support obtained at the end of said step c2) is modified. Preparation of the catalyst is continued by depositing at least one metal from group VIII and optionally at least one metal selected from metals from groups IIIA, IVA, VIIB of the periodic table of the elements onto said zeolitic support in accordance with said step d2). The group VIII metal or metals and optional metal or metals selected from metals from groups IIIA, IVA and VIIB is (are) selected from the list of metals described above for carrying out said step d1) in the first implementation of the preparation of the catalyst of the invention. The precursors of the group VIII metal or metals are analogous to those described above for carrying out said step d1). Said group VIII metal or metals is (are) introduced onto the zeolitic support, namely either mainly onto the modified zeolite by cationic exchange or mainly onto the matrix by anionic exchange or onto the modified zeolite-matrix ensemble by dry impregnation. The protocols for carrying out one or the other of these techniques are analogous to those described above for carrying out said step d1) of the first implementation of the preparation of the catalyst of the invention. When the catalyst comprises at least one metal selected from metals from groups IIIA, IVA and VIIB, the techniques for introducing these metals and the precursors of said metals from groups IIIA, IVA and VIIB are those already described above for carrying out said step d1) of the first implementation of the preparation of the catalyst of the invention.

Preparation of the catalyst in accordance with said second implementation described above is generally terminated by calcining, normally at a temperature in the range 250° C. to 600° C., for a period in the range 0.5 to 10 hours, preferably preceded by drying, for example oven drying, at a temperature from ambient temperature to 250° C., preferably 40° C. to 200° C. Said drying step is preferably carried out during the temperature ramp-up necessary to carry out said calcining. Prior reduction of the catalyst may be carried out ex situ in a stream of hydrogen, for example at a temperature of 450° C. to 600° C., for a period of 0.5 to 4 hours.

In accordance with the third implementation of the preparation of the catalyst of the invention, the as-synthesized EU-1 zeolite obtained in step a3) is then formed with a matrix to prepare a zeolitic support in accordance with said step b3). The as-synthesized EU-1 zeolite is preferably calcined then exchanged before being formed with a matrix, preferably an alumina. However, the forming of step b3) may be carried out directly using as-synthesized EU-1 zeolite, calcining then ion exchange being carried out on the formed zeolite as described for the implementation of the second implementation of the preparation of the catalyst of the invention. Calcining carried out to eliminate the organic template present in the micropores of the EU-1 zeolite prepared in step a3) then ion exchange are carried out under conditions analogous to those described for carrying out said first implementation of the preparation of the catalyst of the invention. The matrix used, preferably an alumina, and the protocol for implementing forming (mixing, extrusion, drying and calcining) are analogous to that described for carrying out step c1) of the first implementation of the preparation of the catalyst of the invention. Advantageously, the EU-1 zeolite associated with the matrix is formed into beads or extrudates, highly advantageously into the form of extrudates, and constitutes the zeolitic support of the catalyst. The preparation of the catalyst in accordance with the third implementation of the invention is continued by depositing at least one group VIII metal and optionally at least one metal selected from metals from groups IIIA, IVA and VIIB of the periodic table of the elements onto said zeolitic support from said step c3). The group VIII metal or metals and optional metal or metals selected from metals from groups IIIA, IVA and VIIB is (are) selected from the list(s) of metals described above for carrying out said step d1) of the first implementation of the preparation of the catalyst of the invention. Preferably, the group VIII metal is platinum. The precursors of the metal or metals from group VIII are analogous to those described above for carrying out said step d1). Said group VIII metal or metals is (are) introduced onto the zeolitic support, namely either mainly onto the zeolite by cation exchange, or mainly onto the matrix by anion exchange or mainly onto the zeolite-matrix ensemble by dry impregnation. The protocols for carrying out one or other of these deposition techniques are analogous to those described above for carrying out said step d1) of the first implementation of the preparation of the catalyst of the invention. When the catalyst comprises at least one metal selected from metals from groups IIIA, IVA and VIIB, the techniques for introducing these metals and the precursors of said metals from groups IIIA, IVA and VIIB are those already described above for carrying out said step d1) of the first implementation of the preparation of the catalyst of the invention. The catalyst obtained is calcined, normally at a temperature in the range 250° C. to 600° C., for a period in the range 0.5 to 10 hours, preferably after having been dried, for example in an oven, at a temperature from ambient temperature to 250° C., preferably 40° C. to 200° C. Said drying step is preferably carried out during the temperature ramp-up necessary for carrying out said calcining step. Optionally, prior reduction of the catalyst may be carried out ex situ in a stream of hydrogen, for example at a temperature of 450° C. to 600° C., for a period of 0.5 to 4 hours, said reduction step being carried out following calcining of the catalyst obtained in step c3).

At the end of said step c3), the catalyst prepared using said third implementation comprises at least one matrix, preferably alumina, at least one metal from group VIII, preferably platinum, and at least one EU-1 zeolite. The zeolitic framework of the EU-1 zeolite is modified so that the extra-lattice hexacoordinated aluminium atoms represent more than 20% by weight of the total number of aluminium atoms present in the EU-1 zeolite in the final catalyst during said step c3) by subjecting the catalyst obtained at the end of said step c3) to a heat treatment in the presence of steam. Advantageously, the heat treatment in the presence of steam is carried out at a temperature in the range 200° C. to 470° C., preferably in the range 320° C. to 460° C. The duration of said heat treatment is generally 0.5 hours or more, preferably in the range 0.5 hours to 24 hours, and highly preferably in the range 1 hour to 12 hours. The percentage by volume of steam during the heat treatment is generally in the range 5% to 100%, preferably in the range 20% to 100%, and more preferably in the range 40% to 100%. The volume fraction other than steam which may be present is formed by air. The flow rate of gas formed by steam and optionally by air is in the range 0.2 l/h/g of solid to 10 l/h/g of solid. The heat treatment in the presence of steam may be repeated as many times as is necessary to obtain the modified EU-1 zeolite with the desired characteristics, in particular a number of hexacoordinated aluminium atoms representing more than 20% by weight of the total number of aluminium atoms present in said zeolite. The number of heat treatments in accordance with said step d3) is preferably less than 4, and advantageously a single heat treatment step is carried out in said step d3).

To prepare the catalyst of the invention, said first implementation and said third implementation are preferred. Highly preferably, the catalyst of the invention is produced by carrying out said third implementation. Said third implementation for the preparation of the catalyst of the invention is particularly advantageous when the heat treatment step d3) is carried out in situ, i.e. when the catalyst obtained at the end of said step c3) is introduced into a catalytic reactor carrying out transformation of a hydrocarbon feed, in particular into a reactor carrying out isomerization of an aromatic feed containing at least one aromatic compound containing eight carbon atoms per molecule. The EU-1 zeolite in the catalyst of the invention is thus modified in situ. Said step d3), when it is carried out in situ, is generally followed by drying the catalyst at a temperature which is preferably in the range 100° C. to 300° C., preferably followed by a reduction in a stream of hydrogen, which is advantageously followed by sulphurization carried out under the conditions described above.

Regardless of the implementation used to prepare the catalyst of the invention, prior reduction of the final catalyst may be carried out ex situ in a stream of hydrogen, for example at a temperature of 450° C. to 600° C., for a period of 0.5 to 4 hours.

In the case in which the catalyst does not contain any sulphur, reduction of the metal in hydrogen is carried out in situ before injecting the feed.

In the case in which the catalyst of the invention contains sulphur, sulphur is introduced onto the catalyst which has been formed and calcined, containing the metal or metals cited above, either in situ before the catalytic reaction or ex situ. Any sulphurization is carried out after reduction. In the case of in situ sulphurization, if the catalyst has not already been reduced, reduction is carried out before sulphurization. In the case of ex situ sulphurization, reduction is carried out followed by sulphurization. Sulphurization is carried out in the presence of hydrogen using any sulphurizing agent which is well known to the skilled person, such as dimethyldisulphide or hydrogen sulphide. As an example, the catalyst is treated with a feed containing dimethyldisulphide in the presence of hydrogen, in a concentration so that the sulphur/metal atomic ratio is 1.5. The catalyst is then maintained for about 3 hours at about 400° C. in a stream of hydrogen before injecting the feed.

The present invention also pertains to a process for isomerizing a cut containing at least one aromatic compound containing eight carbon atoms per molecule, said process comprising bringing said aromatic cut into contact with at least said catalyst in accordance with the invention present in a catalytic reactor. In particular, said aromatic cut containing at least one aromatic compound containing eight carbon atoms per molecule comprises either solely a mixture of xylenes or solely ethylbenzene, or a mixture of xylenes and ethylbenzene. Said isomerization process of the invention is generally carried out under the following operating conditions:
- a temperature in the range 300° C. to 500° C., preferably in the range 320° C. to 450° C. and more preferably in the range 340° C. to 430° C.;
- a partial pressure of hydrogen in the range 0.3 to 1.5 MPa, preferably in the range 0.4 to 1.2 MPa and more preferably in the range 0.7 to 1.2 MPa;
- a total pressure in the range 0.45 to 1.9 MPa, preferably in the range 0.6 to 1.5 MPa; and
- a space velocity, expressed in kilograms of feed introduced per kilogram of catalyst per hour, in the range 0.25 to 30 $h^{-1}$, preferably in the range 1 to 10 $h^{-1}$ and more preferably in the range 2 to 6 $h^{-1}$.

In accordance with the isomerization process of the invention, the catalyst used to carry out said process may be introduced into the catalytic reactor either when the EU-1 zeolite included in said catalyst has already been modified in accordance with the present invention or when it has not yet been modified. In the latter case, modification of the zeolitic framework of the EU-1 zeolite is carried out when the catalyst comprising at least one matrix, preferably alumina, at least one group VIII metal, preferably platinum, and at least one EU-1 zeolite wherein at most 90% by weight of the aluminium atoms are tetracoordinated aluminium atoms is introduced into the catalytic reactor. The heat treatment in the presence of steam, carried out to modify the EU-1 zeolite present in the catalyst loaded into the reactor, is carried out prior to bringing the catalyst of the invention into contact with the aromatic cut to be isomerized. The heat treatment in the presence of steam is thus carried out in situ by passing a stream of steam, optionally supplemented with air, into the catalytic reactor over the catalyst present therein which comprises a EU-1 zeolite which has not yet been modified. The EU-1 zeolite present in the catalyst has been modified by a heat treatment in the presence of steam, said treatment being carried out in situ and prior to bringing the catalyst of the invention into contact with the aromatic cut to be isomerized. When carried out in situ, said heat treatment in the presence of steam is carried out under the same operating conditions as those described above for carrying out heat treatment in the presence of steam in the first implementation for the preparation of the catalyst, the second implementation for the preparation of the catalyst or the third implementation when said treatment is carried out ex situ. Said heat treatment in the presence of steam carried out in situ is preferably followed by drying the catalyst at a temperature which is preferably in the range 100° C. to 300° C., which is preferably followed by a reduction in a stream of hydrogen, which is itself optionally followed by sulphurization.

The following examples illustrate the invention without in any way limiting its scope.

For the MAS-NMR analyses which can characterize and quantify the tetracoordinated aluminium atoms and hexacoordinated aluminium atoms, a Brucker Avance 400 MHz spectrometer with a 4 mm probe optimized for $^{27}Al$ was used. The rotation rate of each sample analyzed was close to 14 kHz. The aluminium atom is a quadripolar nucleus with a spin of 5/2. The analysis conditions were as follows: radiofrequency fields of 30 kHz, pulse angle of $\pi/2$ and water saturation of the analyzed sample. Each MAS-NMR spectrum was calibrated for chemical displacement with respect to a 1M solution of aluminium nitrate for which the aluminium signal was at zero ppm.

EXAMPLE 1

Not in Accordance with the Invention: Preparation of an EU-1 Zeolite

The starting material used was an as-synthesized EU-1 zeolite comprising the organic template, namely 1,6-N,N,N,N',N',N',-hexamethylhexamethylene diammonium, which had an overall Si/Al atomic ratio of 15.3, and a sodium weight content corresponding to a Na/Al atomic ratio (as a %) of 30.8. This EU-1 zeolite had been synthesized in accordance with the teaching of EP-B1-0 042 226. To prepare such a zeolite, the reaction mixture had the following molar composition: 60 $SiO_2$: 10.6 $Na_2O$; 5.27 NaBr: 1.5 $Al_2O_3$: 19.5 Hexa-$Br_2$: 2777$H_2O$. Hexa-$Br_2$ was 1,6-N,N,N,N',N',N',-hexamethylhexamethylene diammonium; bromine was the counterion. The reaction mixture was placed in a stirred autoclave (300 rpm) for 5 days at 180° C.

This EU-1 zeolite initially underwent dry calcining at 550° C. in a stream of dry air for 10 hours to eliminate the organic template. Next, the solid obtained underwent four ion exchanges in a 10N $NH_4NO_3$ solution at about 100° C. for 4 hours for each exchange. The solid obtained was denoted EU-1 (1) and had a Si/Al ratio of 15.3 and a Na/Al ratio of 0.51%.

MAS-NMR analysis of this zeolite allowed the percentage by weight of the tetracoordinated aluminium atoms present in said EU-1 zeolite (1) to be calculated: it was 100%. No hexacoordinated aluminium atoms could be discerned in the MAS-NMR spectrum.

EXAMPLE 2

In Accordance with the Invention: Preparation of a Modified EU-1 Zeolite

The EU-1 zeolite (1) obtained in Example 1 was placed in a furnace where it underwent a hydrothermal treatment: a gas stream constituted by 50% by volume of steam and 50% by volume of air was flushed over said zeolite at 450° C. for 2 hours. The flow rate of the gas was 1 l/h/g of zeolite.

At the end of this hydrothermal treatment, a modified EU-1 zeolite was obtained, denoted EU-1 (2), which was in its hydrogen form. Said EU-1 zeolite (2) had an overall Si/Al atomic ratio equal to that of the EU-1 zeolite (1), namely 15.3. Said EU-1 zeolite (2) was analyzed by MAS-NMR: the MAS-NMR spectrum showed that 23% by weight of aluminium atoms present in the modified EU-1 (2) zeolite were hexacoordinated aluminium atoms and that 77% by weight of the aluminium atoms present in the modified EU-1 zeolite (2) were tetracoordinated aluminium atoms.

EXAMPLE 3

In Accordance with the Invention: Preparation of a Modified EU-1 Zeolite

The EU-1 zeolite (1) obtained in Example 1 was placed in a furnace where it underwent a hydrothermal treatment: a gas stream constituted by 50% by volume of steam and 50% by volume of air was flushed over said zeolite at 350° C. for 8 hours. The flow rate of the steam was 1 l/h/g of zeolite.

At the end of this hydrothermal treatment, a modified EU-1 zeolite was obtained, denoted EU-1 (3), which was in its hydrogen form. Said EU-1 zeolite (3) had an overall Si/Al atomic ratio equal to that of the EU-1 zeolite (1), namely 15.3. Said EU-1 zeolite (3) was analyzed by MAS-NMR: the MAS-NMR spectrum showed that 46% by weight of aluminium atoms present in the modified EU-1 (3) zeolite were hexacoordinated aluminium atoms and that 54% by weight of the aluminium atoms present in the modified EU-1 zeolite (3) were tetracoordinated aluminium atoms.

EXAMPLE 4

Not in Accordance with the Invention: Preparation of a Catalyst A Comprising an Unmodified EU-1 Zeolite The EU-1 zeolite (1) obtained in Example 1 was then formed by extrusion with an alumina gel to obtain, after drying at a temperature of 100° C. overnight and calcining in dry air brought to a temperature of 450° C. for 4 hours, support S1 which contained 10% by weight of EU-1 zeolite and 90% alumina.

This support S1 underwent anion exchange with hexachloroplatinic acid in the presence of hydrochloric acid as a competing agent, to deposit 0.5% by weight of platinum with respect to the weight of catalyst. The moist solid was then dried at 120° C. for 12 hours and calcined in a flow of dry air at a temperature of 500° C. for one hour.

Catalyst A obtained contained, by weight, 10% of EU-1 zeolite, 89.5% of alumina and 0.5% of platinum.

EXAMPLE 5

In Accordance with the Invention: Preparation of a Catalyst B Comprising a Modified EU-1 Zeolite The EU-1 zeolite (2) obtained in Example 2 was then formed by extrusion with an alumina gel to obtain, after drying at a temperature of 100° C. overnight and calcining in dry air brought to a temperature of 450° C. for 4 hours, support S2 which contained 10% by weight of modified EU-1 zeolite and 90% alumina.

This support S2 underwent anion exchange with hexachloroplatinic acid in the presence of hydrochloric acid as a competing agent, to deposit 0.5% by weight of platinum with respect to the weight of catalyst. The moist solid was then dried at 120° C. for 12 hours and calcined in a flow of dry air at a temperature of 500° C. for one hour.

Catalyst B obtained contained, by weight, 10% of modified EU-1 zeolite, 89.5% of alumina and 0.5% of platinum.

EXAMPLE 6

In Accordance with the Invention: Preparation of a Catalyst C Comprising a Modified EU-1 Zeolite The EU-1 zeolite (3) obtained in Example 3 was then formed by extrusion with an alumina gel to obtain, after drying at a temperature of 100° C. overnight and calcining in dry air brought to a temperature of 450° C. for 4 hours, the support S3 which contained 10% by weight of modified EU-1 zeolite and 90% alumina.

This support S3 underwent anion exchange with hexachloroplatinic acid in the presence of hydrochloric acid as a competing agent, to deposit 0.5% by weight of platinum with respect to the weight of catalyst. The moist solid was then dried at 120° C. for 12 hours and calcined in a flow of dry air at a temperature of 500° C. for one hour.

Catalyst C obtained contained, by weight, 10% of modified EU-1 zeolite, 89.5% of alumina and 0.5% of platinum.

EXAMPLE 7

Evaluation of Catalytic Properties of Catalysts A, B and C for the Isomerization of Ethylbenzene The feed to be isomerized, brought into contact with catalyst A, with catalyst B then with catalyst C, was constituted solely by ethylbenzene.

The operating conditions for the isomerization reaction were as follows:
 temperature: 410° C.;
 total pressure: 10 bars (1 bar=0.1 MPa);
 partial pressure of hydrogen: 8 bars;
 feed: ethylbenzene;
 space velocity, expressed in kilograms of feed introduced per kilogram of catalyst per hour, of 8.7 $h^{-1}$.

The catalytic properties of catalysts A, B and C were evaluated in succession for the isomerization of ethylbenzene. Each catalyst was reduced in hydrogen for 4 hours at 480° C. before injecting the feed.

The catalysts were evaluated in terms of ethylbenzene conversion and xylene selectivity.

The selectivity for xylenes was calculated using the yield of the xylenes produced. The yield of xylenes was determined from the % by weight of xylenes produced, obtained by analysis of each effluent.

The conversion of ethylbenzene was the percentage of ethylbenzene consumed.

TABLE 1

Conversion of ethylbenzene and selectivity for xylenes on catalysts A, B and C after 4000 min of reaction

|  | Catalyst A | Catalyst B | Catalyst C |
|---|---|---|---|
| Ethylbenzene conversion (%) | 28.6 | 41.8 | 42.3 |
| Xylene selectivity (%) | 68.1 | 68.1 | 68.1 |
| Xylenes yield (%) | 19.5 | 28.5 | 28.8 |

The results shown in Table 1 show that catalysts B and C each comprising a modified EU-1 zeolite in which the number of extra-lattice hexacoordinated aluminium atoms represent more than 20% by weight of the total number of aluminium atoms present in each of said modified zeolites, produced much better catalytic performances in terms of ethylbenzene conversion than that obtained using catalyst A comprising an unmodified EU-1 zeolite. Catalysts B and C of the invention were thus substantially more active than prior art catalyst A.

Further, catalysts B and C in accordance with the invention produced a xylenes selectivity identical to that obtained with catalyst A; as a result, catalysts B and C in accordance with the invention produced a yield of xylenes which was much higher than the yield of xylenes obtained with the comparative catalyst A, the yield of xylenes being the product of the ethylbenzene conversion and the xylenes selectivity.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French application Ser. No. 07/02943, filed Apr. 23, 2007, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A catalyst comprising at least one modified EU-1 zeolite containing silicon atoms and aluminium atoms, at least one matrix and at least one metal from group VIII of the periodic table of the elements, said catalyst being characterized in that the number of hexacoordinated aluminium atoms present in said modified zeolite represents more than 20% by weight of the total number of aluminium atoms present in said modified EU-1 zeolite.

2. A catalyst according to claim 1, in which said modified EU-1 zeolite has a number of hexacoordinated aluminium atoms representing more than 22% by weight of the total number of aluminium atoms present in said modified zeolite.

3. A catalyst according to claim 1, in which said modified EU-1 zeolite has a number of hexacoordinated aluminium atoms representing more than 25% by weight of the total number of aluminium atoms present in said modified zeolite.

4. A catalyst according to claim 1, in which said modified EU-1 zeolite has a number of hexacoordinated aluminium atoms representing more than 30% by weight of the total number of aluminium atoms present in said modified zeolite.

5. A catalyst according to claim 4, in which said modified EU-1 zeolite has an overall Si/Al atomic ratio in the range 10 to 35.

6. A catalyst according to claim 5, in which said group VIII metal is platinum.

7. A catalyst according to claim 6, comprising sulphur.

8. A catalyst according to claim 7, in which said matrix is an alumina.

9. A catalyst according to claim 1, in which said modified EU-1 zeolite has an overall Si/Al atomic ratio in the range 10 to 35.

10. A catalyst according to claim 1, in which said group VIII metal is platinum.

11. A catalyst according to claim 1, comprising at least one additional metal selected from the group formed by metals from groups IIIA, IVA and VIIB.

12. A catalyst according to claim 1, comprising sulphur.

13. A catalyst according to claim 1, in which said matrix is an alumina.

14. A catalyst according to claim 1, in which it is in the form of extrudates.

15. A process for preparing a catalyst according to claim 1, comprising at least the following steps:
   a1) synthesizing at least one EU-1 zeolite having an overall Si/Al atomic ratio in the range 5 to 100;
   b1) heat treating the zeolite from said step a1) in the presence of steam to obtain a modified EU-1 zeolite;
   c1) forming said modified EU-1 zeolite with a matrix to form a modified zeolitic support;
   d1) depositing at least one metal from group VIII of the periodic table of the elements, the order of carrying out said steps c1) and d1) being inconsequential following upon said step b1).

16. A preparation process according to claim 15, in which said heat treatment in the presence of steam is carried out at a temperature in the range 200° C. to 470° C., for a period in the range 0.5 hours to 24 hours, the percentage by volume of steam being in the range 5% to 100%.

17. A catalyst produced by the process of claim 16.

18. A preparation process according to claim 15, in which said step c1) precedes said step d1).

19. A process for preparing a catalyst according to claim 1, comprising at least the following steps:
   a2) synthesizing at least one EU-1 zeolite having an overall Si/Al atomic ratio in the range 5 to 100;
   b2) forming the EU-1 zeolite from said step a2) with a matrix to form a zeolitic support;
   c2) heat treating the zeolitic support formed in step b2) in the presence of steam;
   d2) depositing at least one metal from group VIII of the periodic table of the elements on the modified zeolitic support of step c2).

20. A process for preparing a catalyst according to claim 1, comprising at least the following steps:
   a3) synthesizing at least one EU-1 zeolite having an overall Si/Al atomic ratio in the range 5 to 100;
   b3) forming the EU-1 zeolite from said step a3) with a matrix to form a zeolitic support;

c3) depositing at least one metal from group VIII of the periodic table of the elements on the zeolitic support from said step b3);

d3) heat treating the zeolitic support impregnated with at least said group VIII metal from said step c3) in the presence of steam.

21. A process for isomerizing a cut containing at least one aromatic compound containing eight carbon atoms per molecule, said process comprising bringing said aromatic cut into contact with at least one catalyst comprising a modified zeolite according to claim 1, present in a catalytic reactor.

22. An isomerization process according to claim 21, carried out under the following operating conditions: a temperature in the range 300° C. to 500° C., a partial pressure of hydrogen in the range 0.3 to 1.5 MPa, a total pressure in the range 0.45 to 1.9 MPa and a space velocity, expressed in kilograms of feed introduced per kilogram of catalyst per hour, in the range 0.25 to 30 $h^{-1}$.

23. An isomerization process according to claim 21, in which the EU-1 zeolite present in said catalyst has been modified by a heat treatment in the presence of steam, said treatment being carried out in situ and prior to bringing said catalyst into contact with said aromatic cut.

* * * * *

UNITED STATES PATENT AND TRADEMARK OFFICE
CERTIFICATE OF CORRECTION

| | | |
|---|---|---|
| PATENT NO. | : 7,838,456 B2 | |
| APPLICATION NO. | : 12/107224 | |
| DATED | : November 23, 2010 | |
| INVENTOR(S) | : Guillon et al. | |

It is certified that error appears in the above-identified patent and that said Letters Patent is hereby corrected as shown below:

Title page item (75) Inventors:, line 2 reads "Erie Sanchez, Saint Genis Laval (FR)" should read
-- Eric Sanchez, Saint Genis Laval (FR) --.

Signed and Sealed this
First Day of February, 2011

David J. Kappos
*Director of the United States Patent and Trademark Office*